(12) United States Patent
Mazzuca et al.

(10) Patent No.: US 9,566,169 B2
(45) Date of Patent: Feb. 14, 2017

(54) ACIS ALLOGRAFT DESIGNS

(71) Applicant: DePuy Synthes Products, Inc., Raynham, MA (US)

(72) Inventors: Michael Mazzuca, North Easton, MA (US); Thomas Gamache, Westport, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 91 days.

(21) Appl. No.: 14/208,910

(22) Filed: Mar. 13, 2014

(65) Prior Publication Data

US 2015/0257893 A1    Sep. 17, 2015

(51) Int. Cl.
*A61F 2/44*    (2006.01)
*A61F 2/30*    (2006.01)

(52) U.S. Cl.
CPC ............. *A61F 2/447* (2013.01); *A61F 2/4455* (2013.01); *A61F 2002/30057* (2013.01); *A61F 2002/30383* (2013.01); *A61F 2002/30492* (2013.01); *A61F 2250/006* (2013.01); *A61F 2250/0062* (2013.01); *A61F 2250/0063* (2013.01); *A61F 2310/00359* (2013.01)

(58) Field of Classification Search
CPC ................................ A61F 2/4455; A61F 2/447
See application file for complete search history.

(56) References Cited

U.S. PATENT DOCUMENTS

| | | | |
|---|---|---|---|
| 4,678,470 A | 7/1987 | Nashef | |
| 6,200,347 B1 * | 3/2001 | Anderson | A61F 2/28 623/11.11 |
| 6,379,385 B1 | 4/2002 | Kalas | |
| 6,398,811 B1 | 6/2002 | McKay | |
| 6,511,509 B1 | 1/2003 | Ford | |
| 6,635,087 B2 | 10/2003 | Angelucci | |
| 6,638,310 B2 | 10/2003 | Lin | |
| 6,706,067 B2 | 3/2004 | Shimp | |
| 6,761,739 B2 * | 7/2004 | Shepard | A61F 2/28 623/17.16 |
| 7,018,412 B2 | 3/2006 | Ferreira | |
| 7,018,416 B2 | 3/2006 | Hanson | |
| 7,060,096 B1 | 6/2006 | Schopf | |
| 7,135,042 B2 | 11/2006 | Stoll | |
| 7,163,560 B2 | 1/2007 | Mason | |
| 7,201,775 B2 | 4/2007 | Gorensek | |
| 7,252,685 B2 | 8/2007 | Bindseil | |
| 7,311,734 B2 | 12/2007 | Van Hoeck | |
| 7,323,011 B2 * | 1/2008 | Shepard | A61F 2/447 623/17.11 |
| 7,618,460 B2 | 11/2009 | Boyd | |
| 7,621,960 B2 | 11/2009 | Boyd | |
| 7,662,185 B2 | 2/2010 | Alfaro | |
| 7,726,002 B2 | 6/2010 | Shimp | |
| 7,833,271 B2 | 11/2010 | Mitchell | |
| 7,998,212 B2 | 8/2011 | Schwab | |
| 8,012,210 B2 | 9/2011 | Lin | |
| 8,043,377 B2 | 10/2011 | Guyer | |
| 8,043,380 B1 | 10/2011 | Park | |
| 8,062,372 B2 | 11/2011 | Tsuang | |

(Continued)

*Primary Examiner* — Andrew Yang

(57) ABSTRACT

Structural allograft fusion devices containing a single integral piece of cortical bone in combination with one or more pieces of cancellous bone, wherein the cortical and cancellous pieces are pinned together.

40 Claims, 9 Drawing Sheets

(56) References Cited

U.S. PATENT DOCUMENTS

| | | |
|---|---|---|
| 8,182,532 B2 | 5/2012 | Anderson |
| 8,252,055 B2 | 8/2012 | McKay |
| 8,291,572 B2 | 10/2012 | Grooms |
| 8,435,302 B2 | 5/2013 | Ulrich, Jr. |
| 8,454,696 B2 | 6/2013 | Borden |
| 8,480,715 B2 | 7/2013 | Gray |
| 8,523,947 B2 | 9/2013 | Theofilos |
| 9,039,768 B2* | 5/2015 | Voellmicke ............ A61F 2/4455 606/86 A |
| 2005/0049706 A1* | 3/2005 | Brodke ................ A61F 2/30767 623/17.11 |
| 2005/0107879 A1* | 5/2005 | Christensen ........... A61L 27/306 623/17.11 |
| 2009/0088765 A1* | 4/2009 | Butler .................... A61F 2/4455 606/90 |
| 2010/0042218 A1 | 2/2010 | Nebosky |
| 2011/0313538 A1 | 12/2011 | Oh |
| 2012/0172998 A1 | 7/2012 | Oishi |
| 2012/0185047 A1 | 7/2012 | Wooley |
| 2012/0330420 A1* | 12/2012 | Brodke ............... A61F 2/30767 623/17.16 |
| 2013/0073047 A1 | 3/2013 | Laskowitz |
| 2013/0110238 A1 | 5/2013 | Lindemann |
| 2015/0230937 A1* | 8/2015 | Voellmicke ............. A61F 2/442 623/17.16 |

* cited by examiner

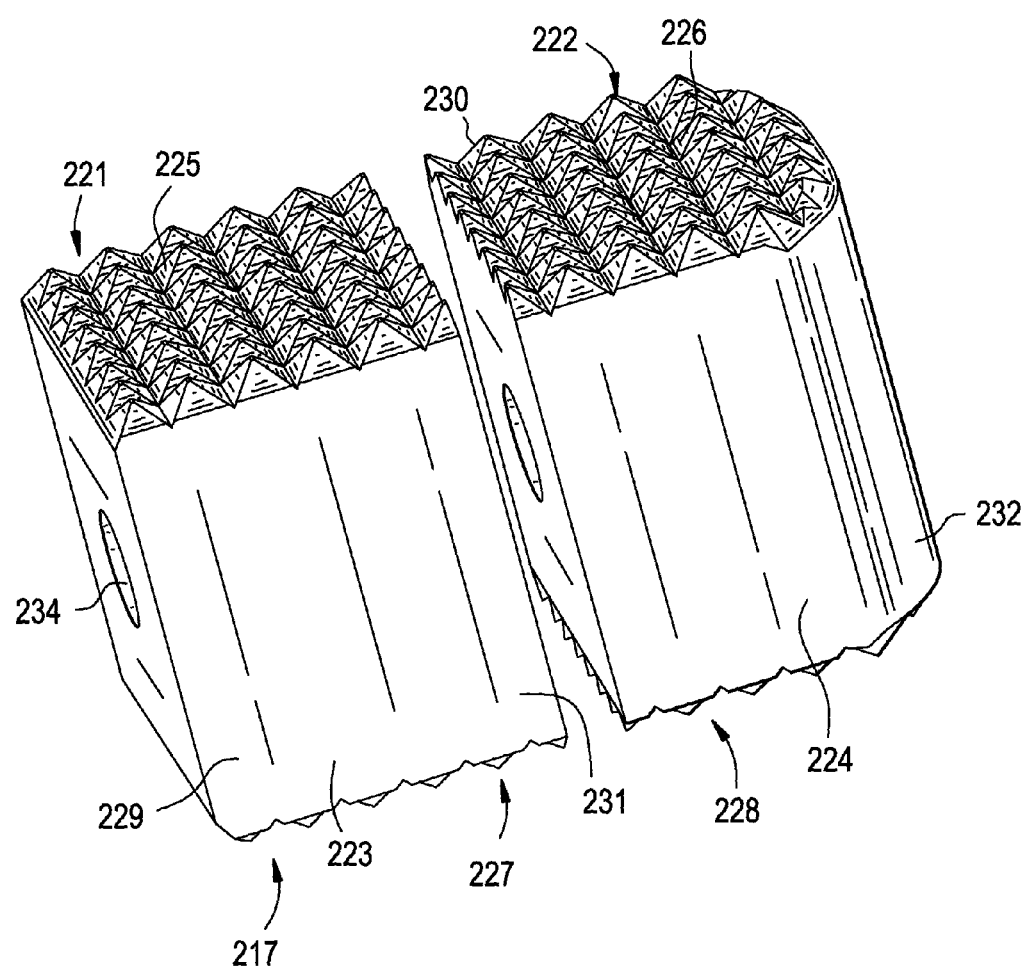

ACIS ALLOGRAFT DESIGNS

BACKGROUND OF THE INVENTION

The natural intervertebral disc contains a jelly-like nucleus pulposus surrounded by a fibrous annulus fibrosus. Under an axial load, the nucleus pulposus compresses and radially transfers that load to the annulus fibrosus. The laminated nature of the annulus fibrosus provides it with a high tensile strength and so allows it to expand radially in response to this transferred load.

In a healthy intervertebral disc, cells within the nucleus pulposus produce an extracellular matrix (ECM) containing a high percentage of proteoglycans. These proteoglycans contain sulfated functional groups that retain water, thereby providing the nucleus pulposus within its cushioning qualities. These nucleus pulposus cells may also secrete small amounts of cytokines such as interleukin-1β and TNF-α as well as matrix metalloproteinases ("MMPs"). These cytokines and MMPs help regulate the metabolism of the nucleus pulposus cells.

In some instances of disc degeneration disease (DDD), gradual degeneration of the intervetebral disc is caused by mechanical instabilities in other portions of the spine. In these instances, increased loads and pressures on the nucleus pulposus cause the cells within the disc (or invading macrophases) to emit larger than normal amounts of the above-mentioned cytokines. In other instances of DDD, genetic factors or apoptosis can also cause the cells within the nucleus pulposus to emit toxic amounts of these cytokines and MMPs. In some instances, the pumping action of the disc may malfunction (due to, for example, a decrease in the proteoglycan concentration within the nucleus pulposus), thereby retarding the flow of nutrients into the disc as well as the flow of waste products out of the disc. This reduced capacity to eliminate waste may result in the accumulation of high levels of toxins that may cause nerve irritation and pain.

As DDD progresses, toxic levels of the cytokines and MMPs present in the nucleus pulposus begin to degrade the extracellular matrix, in particular, the MMPs (as mediated by the cytokines) begin cleaving the water-retaining portions of the proteoglycans, thereby reducing its water-retaining capabilities. This degradation leads to a less flexible nucleus pulposus, and so changes the loading pattern within the disc, thereby possibly causing delamination of the annulus fibrosus. These changes cause more mechanical instability, thereby causing the cells to emit even more cytokines, thereby upregulating MMPs. As this destructive cascade continues and DDD further progresses, the disc begins to bulge ("a herniated disc"), and then ultimately ruptures, causing the nucleus pulposus to contact the spinal cord and produce pain.

One proposed method of managing these problems is to remove the problematic disc and replace it with a porous device that restores disc height and allows for bone growth therethrough for the fusion of the adjacent vertebrae. These devices are commonly called "fusion devices". The goal of a fusion device is to stabilize the motion segment associated with the problematic disc space so that a fusion can occur between the adjacent vertebrae. The conventional fusion device is typically a hollow cage that contains graft material that assists in the formation of new bone. The fusion device provides a bloody pathway between the endplates of the adjacent vertebrae for new bone to form.

Fusion devices can be made from any structural biocompatible material, including metals, polymers, and allograft. Some surgeons prefer to use fusion devices made from allograft because the allograft contains bone morphogenic proteins that induce bone growth behavior from the patient's system.

A number of medical conditions, such as compression of spinal cord nerve roots, degenerative disc disease, and trauma can cause severe back pain. Intervertebral fusion is a surgical method of alleviating back pain. In intervertebral fusion, two adjacent vertebral bodies are fused together by removing the affected intervertebral disc and inserting an implant that would allow for bone to grow between the two vertebral bodies to bridge the gap left by the removed disc.

A number of different implants and implant materials have been used for fusion with varying success. Current implants for intevertebral fusion include metallic cages and allografts. Metallic cages suffer from the disadvantage of requiring drilling and tapping of the vertebral endplates for insertion. In addition, the incidence of subsidence in long term use is not known. Due to MRI incompatibility of metallic cages, determining fusion is problematic.

Allografts are sections of bone taken from the diaphysis of a long bone, such as the radius, ulna, fibula, humerus, tibia, or femur of a donor. A cross-section of the bone is taken and processed using known techniques to preserve the allograft until implantation and reduce the risk of an adverse immunological response when implanted. For example, U.S. Pat. No. 4,678,470 discloses a method for processing a bone grafting material which uses glutaraldehyde tanning to produce a non-antigenic, biocompatible material. Allografts have mechanical properties which are similar to the mechanical properties of vertebrae even after processing. This prevents stress shielding that occurs with metallic implants. They also promote the formation of bone, i.e., osteoconductive, and are also MRI compatible so that fusion can be more accurately ascertained. Although the osteoconductive nature of the allograft provides a biological interlocking between the allograft and the vertebrae for long term mechanical strength, initial and short term mechanical strength of the interface between the allograft and the vertebrae needs to be addressed to minimize the possibility of the allograft being expelled after implantation.

Most allografts are simply sections of bone which, although cut to the approximate height of the disc being replaced, have not been sized and/or machined on the exterior surface to have a uniform shape. As a result, the fusion of the vertebral bodies does not occur in optimal anatomic position or in a consistent manner along the surface of the endplates. While a surgeon may do some minimal intraoperative shaping and sizing to customize the allograft for the patient's spinal anatomy, significant shaping and sizing of the allograft during the procedure is not possible due to the nature of the allograft. Even if extensive shaping and sizing were possible, a surgeon's ability to manually shape and size the allograft to the desired dimensions is limited.

With respect to the overall structure of a given bone, the mechanical properties vary throughout the bone. For example, a long bone (leg bone) such as the femur has both cortical bone and cancellous bone. Cortical bone, the compact and dense bone that surrounds the marrow cavity, is generally solid and thus carries the majority of the load in long bones. Cancellous bone, the spongy inner bone, is generally porous and ductile, and when compared to cortical bone is only about one-third to one-quarter as dense, one-tenth to one-twentieth as stiff, but five times as ductile. While cancellous bone has a tensile strength of about 10-20 MPa and a density of about 0.7, cortical bone has a tensile strength of about 100-200 MPa and a density of about 2. Additionally, the strain to failure of cancellous bone is about 5-7%, while cortical bone can only withstand 1-3% strain before failure. It should also be noted that these mechanical characteristics may degrade as a result of numerous factors such as any chemical treatment applied to the bone material, and the manner of storage after harvesting but prior to implantation (i.e. drying of bones).

Notably, implants of cancellous bone incorporate more readily with the surrounding host bone, due to the superior osteoconductive nature of cancellous bone as compared to cortical bone. Furthermore, cancellous bone from different regions of the body is known to have a range of porosities. Thus, the design of an implant using cancellous bone may be tailored to specifically incorporate material of a desired porosity.

U.S. Pat. No. 6,511,509 (Ford) discloses a textured bone allograft for implantation in a patient, having one or more textured bone surfaces, and methods of making and using the textured bone graft. The textured surface preferably includes a plurality of closely spaced discrete, continuous, or a combination thereof, protrusions. The textured bone allograft is useful for repairing bone defects caused by congenital anomaly, disease, or trauma, in a patient, for example, for restoring vertical support of the anterior column. Implantation of the textured bone allograft results in improved graft stability and osteoinductivity, without a decrease in mechanical strength. The textured bone allograft does not shift, extrude or rotate, after implantation. Ford discloses one device having a plank of cancellous bone sandwiched between a pair of separate cortical bone planks.

SUMMARY OF THE INVENTION

The present invention is directed to structural allograft fusion devices containing a single integral piece of cortical bone.

Therefore, in accordance with the present invention, there is provided an allograft composite spacer, comprising:
a) an integral cortical component comprising:
   i. first and second opposing walls, each wall having an upper surface, a lower surface, a first end portion and a second end portion and
   ii. a strut extending from the first end portion of the first cortical wall to the first end portion of the second cortical wall, wherein the strut does not extend to either the upper surface or the lower surface, and
b) a cancellous component having first and second lateral surfaces, an upper surface, a lower surface, a first end have a first end surface, a second end, and a recess in the first end surface extending from the first lateral surface to the second lateral surface,
wherein the strut of the cortical components is received in the recess of the cancellous component.

Also in accordance with the present invention, there is provided an allograft composite spacer, comprising:
a) an integral cortical component comprising:
   i. first and second opposing walls, each wall having an upper surface and a lower surface defining a height therebetween, a first end portion and a second end portion and
   ii. a strut extending from the first end portion of the first cortical wall to the first end portion of the second cortical wall, wherein the strut does not extend to either the upper surface or the lower surface, wherein the strut runs substantially from the first end portion to the second end portion of each opposing wall,
b) upper and lower cancellous components, each having first and second lateral surfaces, an upper surface, a lower surface, a first end have a first end surface, a second end,
wherein the upper cancellous component is received above the strut and between the opposing walls, and
wherein the lower cancellous component is received below the strut and between the opposing walls.

Also in accordance with the present invention, there is provided an allograft composite spacer, comprising:
a) an integral cortical component comprising:
   i. first and second opposing walls, each wall having an upper surface and a lower surface defining a height therebetween, a first end portion and a second end portion and
   ii. a strut extending from the first end portion of the first cortical wall to the first end portion of the second cortical wall, wherein the strut does not extend to either the upper surface or the lower surface, wherein the strut runs substantially from the first end portion to the second end portion of each opposing wall, the strut having a vertical throughhole therethrough
b) upper and lower cancellous components, each having first and second lateral surfaces, an upper surface, a lower surface, a first end have a first end surface, a second end, the upper cancellous component having an extension extending from its lower surface, the lower cancellous component having an extension extending from its upper surface
wherein the upper cancellous component is received substantially above the strut and between the opposing walls, and
wherein the lower cancellous component is received substantially below the strut and between the opposing walls, and
wherein each extension is received in the vertical throughhole.

Also in accordance with the present invention, there is provided an allograft composite spacer, comprising:
a) an integral cortical component comprising:
   i. first and second opposing walls, each wall having an upper surface, a lower surface, a first end portion and a second end portion and
   ii. a strut extending from the first end portion of the first cortical wall to the first end portion of the second cortical wall, wherein the strut does not extend to either the upper surface or the lower surface, and
b) upper and lower cancellous components, each having first and second lateral surfaces, an upper surface, a lower surface, a first end have a first end surface, a second end, the upper cancellous component having a recess on its lower surface running between its lateral surfaces, the lower cancellous component having a recess on its upper surface running between its lateral surfaces,
wherein the upper cancellous component is received between the opposing walls substantially above the strut and its recess receives the strut, and
wherein the lower cancellous component is received between the opposing walls substantially below the strut and its recess receives the strut.

Also in accordance with the present invention, there is provided an allograft composite spacer, comprising:
a) an integral cortical component comprising:
   i. first and second opposing walls, each wall having an upper surface and a lower surface defining a height therebetween, and an anterior end and a posterior end defining a middle third portion therebetween, and ii. a strut extending between the opposing walls and extending substantially to each of the upper surface or the lower surface, and wherein the strut is located only in the middle third portion of the opposing walls, b) first and second cancellous components, each having first and second lateral surfaces, an upper surface, a lower surface, an anterior end and a posterior end, wherein the first cancellous component is received anterior to the strut and between the opposing walls, and wherein the second cancellous component is received posterior to the strut and between the opposing walls.

DESCRIPTION OF THE FIGURES

FIGS. 5A-5C disclose a fifth embodiment of the present invention.

DETAILED DESCRIPTION OF THE PRESENT INVENTION

Ideally, an intervertebral implant comprises as much cancellous bone as possible while providing sufficient support to maintain the proper spacing between the vertebrae being treated, so that the promotion of new bone growth is maximized. By properly sizing and shaping the section of implant composed of cortical bone, and by properly aligning this section so that it is subject to the majority of forces exerted on implant by the vertebrae being treated, the implant has sufficient strength to maintain the proper distance between the vertebrae, while minimizing the amount of cortical bone required. The rest of implant, being composed of cancellous bone can then be used more advantageously to promote the growth of new bone between the vertebrae being treated, thus providing long-term stability to the vertebrae and the implant.

Thus, the implant of the present invention takes advantage of the different properties of cortical and cancellous bone to improve the use of allogenic bone in the surgical method of intervertebral fusion. The implant may be customized according to the needs of the user, as different combinations of cortical and cancellous bone, may be selected, depending upon the properties desired. An implant in accordance with the present invention also allows for more efficient use of available material, as pieces of allogenic bone that would otherwise not be large enough to form a suitably sized implant may be used instead to form a part of the implant.

Figure 1A:
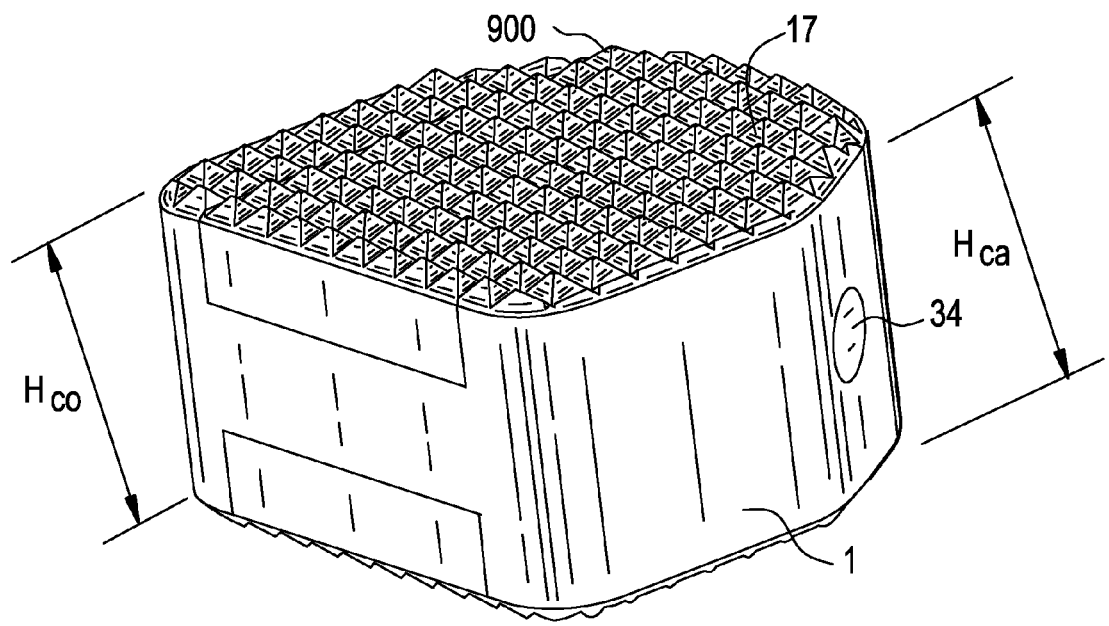
FIGS. 1A-1C disclose a first embodiment of the present invention.
Figure 1B:
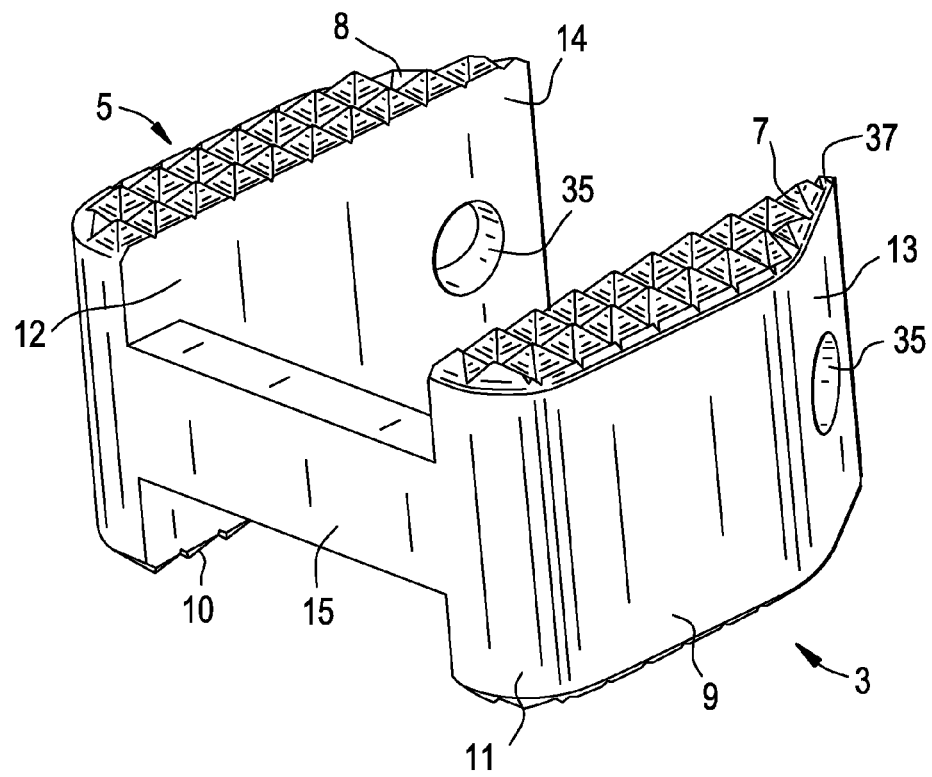
Figure 1C:
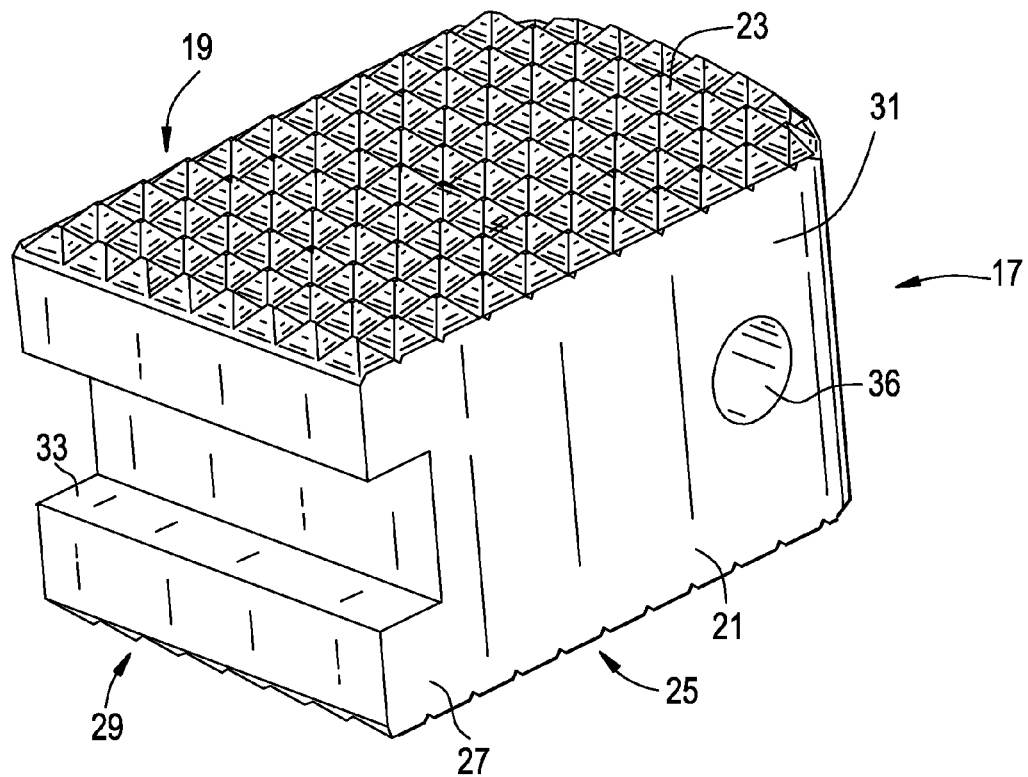

Now referring to FIGS. 1A-1C, there is provided an allograft composite spacer, comprising:

a) an integral cortical component 1 comprising:
  i. first 3 and second 5 opposing walls, each wall having an upper surface 7,8, a lower surface 9,10, a first end portion 11,12 and a second end portion 13,14 and
  ii. a strut 15 extending from the first end portion of the first cortical wall to the first end portion of the second cortical wall, wherein the strut does not extend to either the upper surface or the lower surface, and b) a cancellous component 17 having first 19 and second 21 lateral surfaces, an upper surface 23, a lower surface 25, a first end 27 have a first end surface 29, a second end 31, and a recess 33 in the first end surface extending from the first lateral surface to the second lateral surface, wherein the strut of the cortical components is received in the recess of the cancellous component.

In some embodiments, the second end portions of the first and second opposing walls of the cortical component each include a throughhole 35, wherein the through holes are aligned. Similarly, the cancellous portion has a throughhole 36.

In some embodiments, the spacer further comprises:
  c) an allograft pin 34 inserted into both of the aligned throughholes.

In some embodiments, the second end portion of the first and second opposing walls of the cortical component has a second end face 37, and the second end portion of each opposing sidewall of the cortical component narrows towards the second endface.

In some embodiments, the upper and lower surfaces of the opposing walls of the cortical component each has gripping features thereon.

In some embodiments, the upper and lower surfaces of the cancellous component each has gripping features thereon.

In some embodiments, the upper and lower surfaces of the cortical component define a height Hco therebetween, the upper and lower surfaces of the cancellous component define a height Hca therebetween, and the height of cortical component is substantially equal to the height of the cancellous component.

Figure 2A:
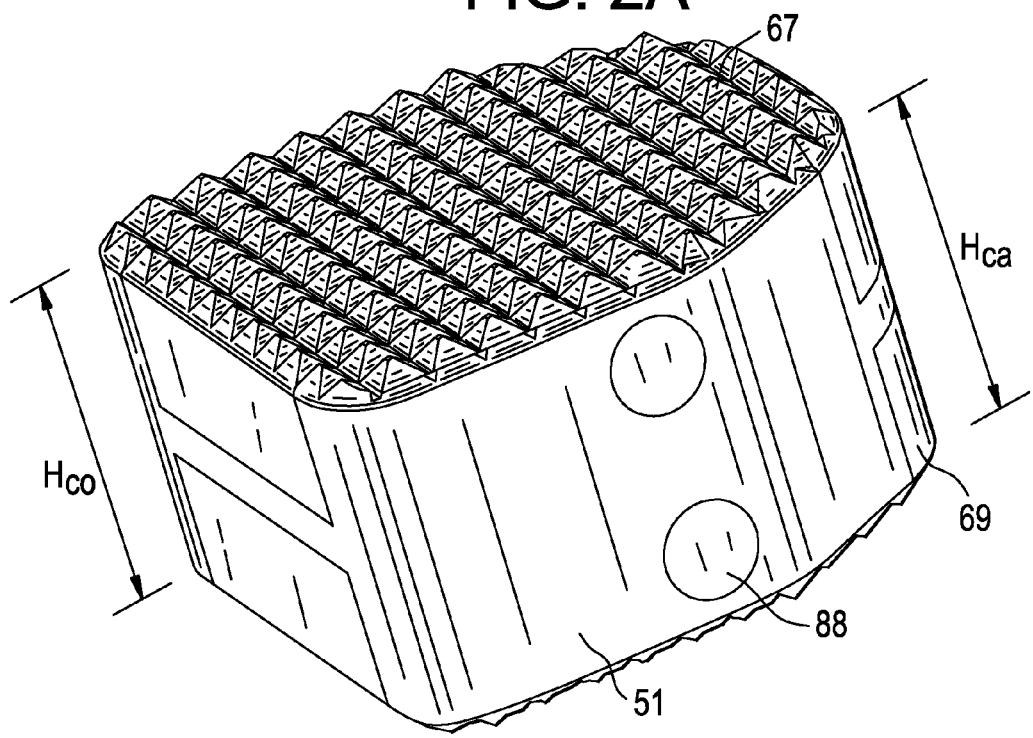
FIGS. 2A-2C disclose a second embodiment of the present invention.
Figure 2B:
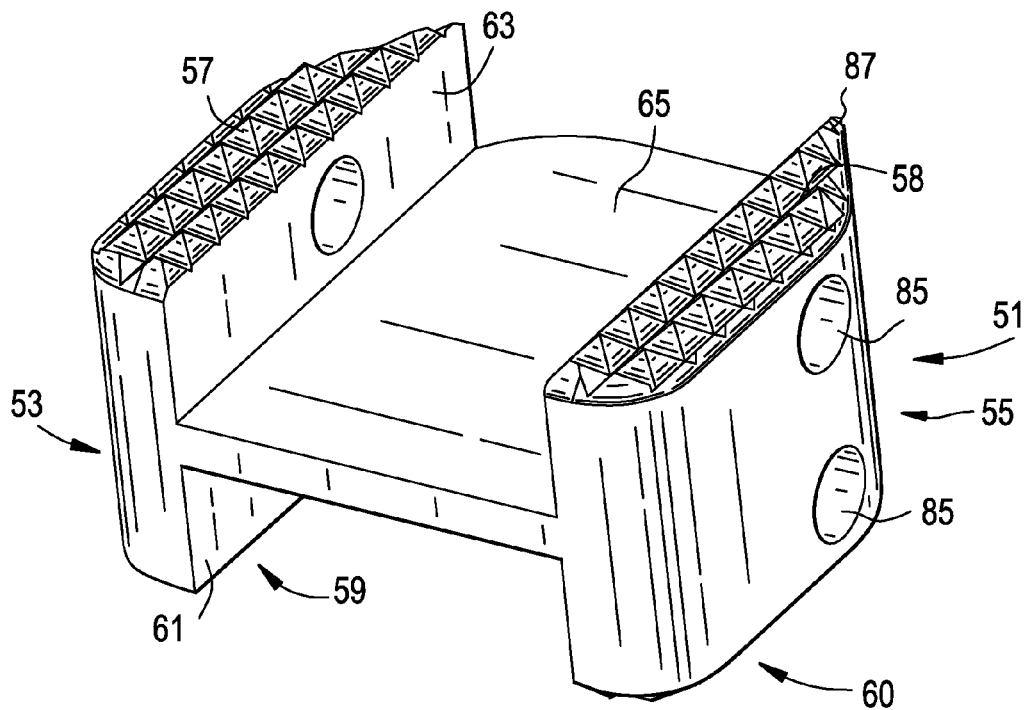
Figure 2C:
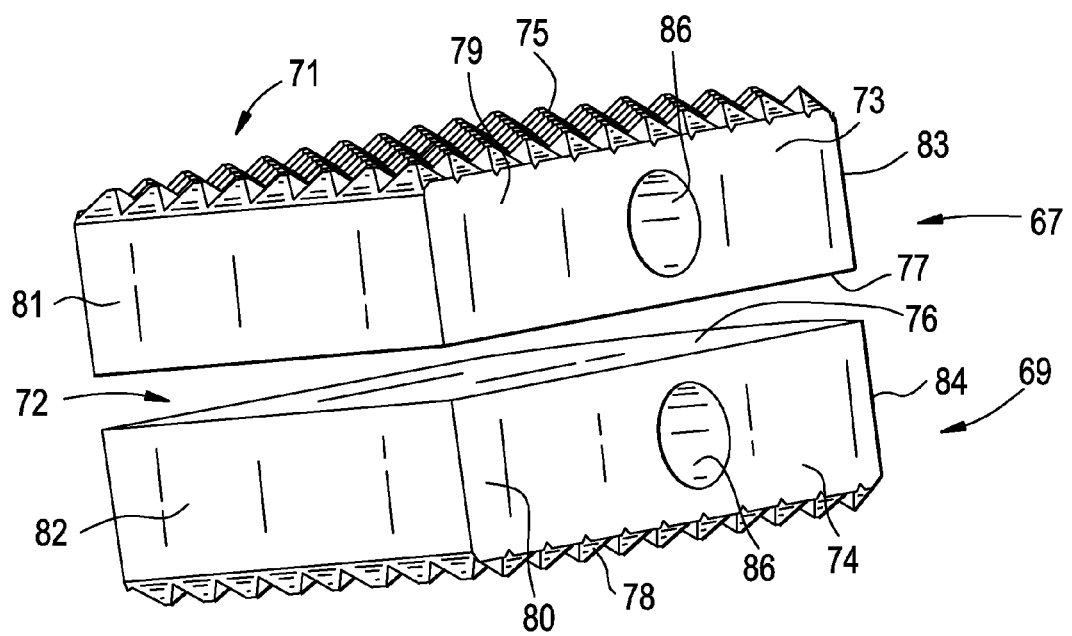
Figure 3A:
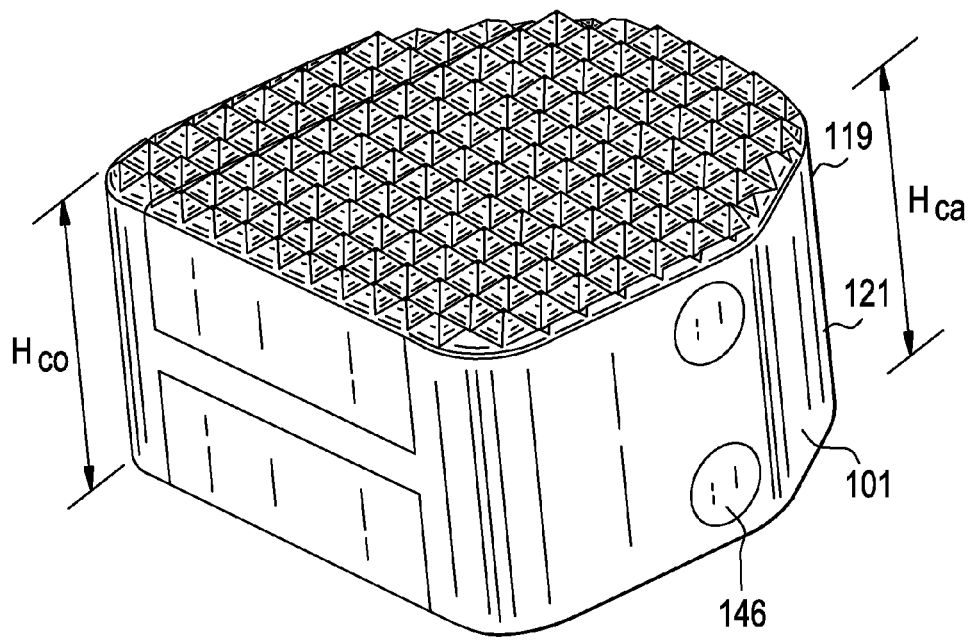
FIGS. 3A-3D disclose a third embodiment of the present invention.
Figure 3B:
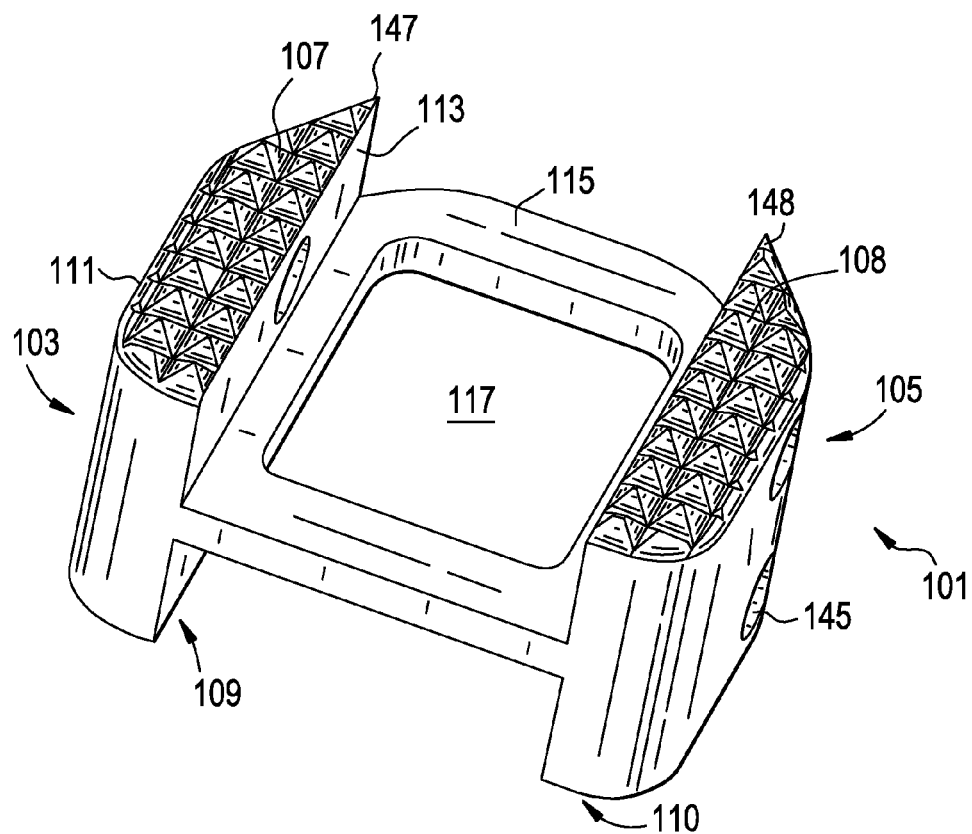
Figure 3C:
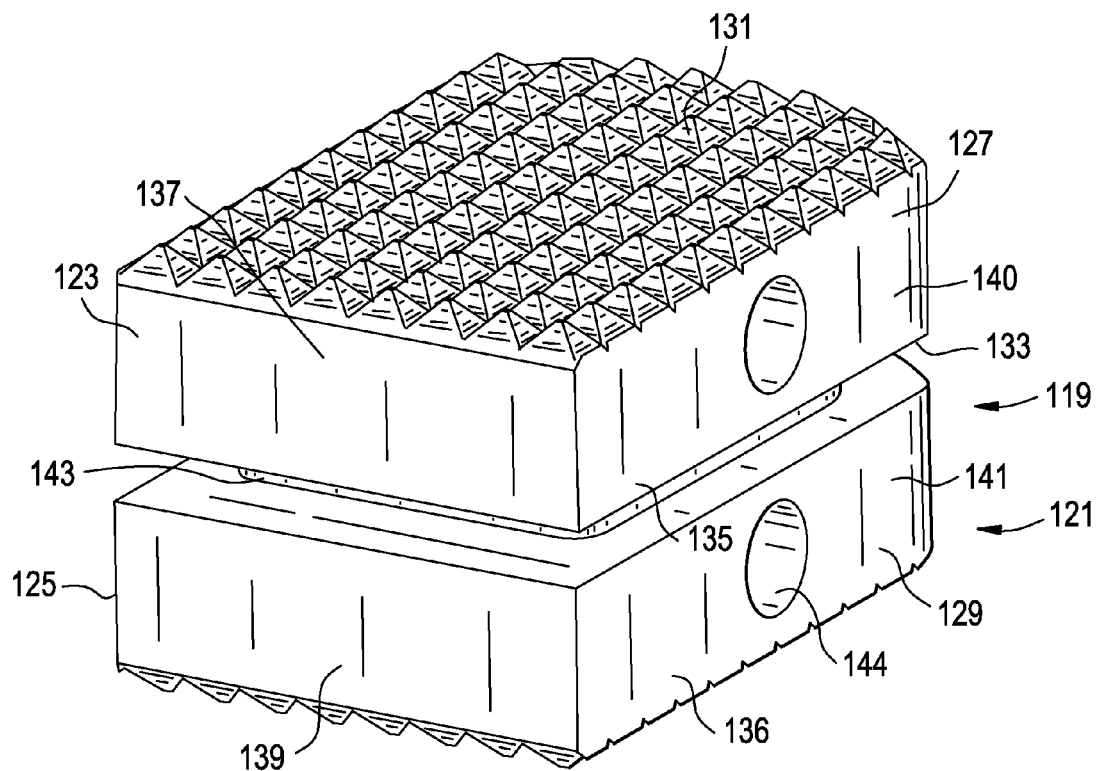
Figure 3D:
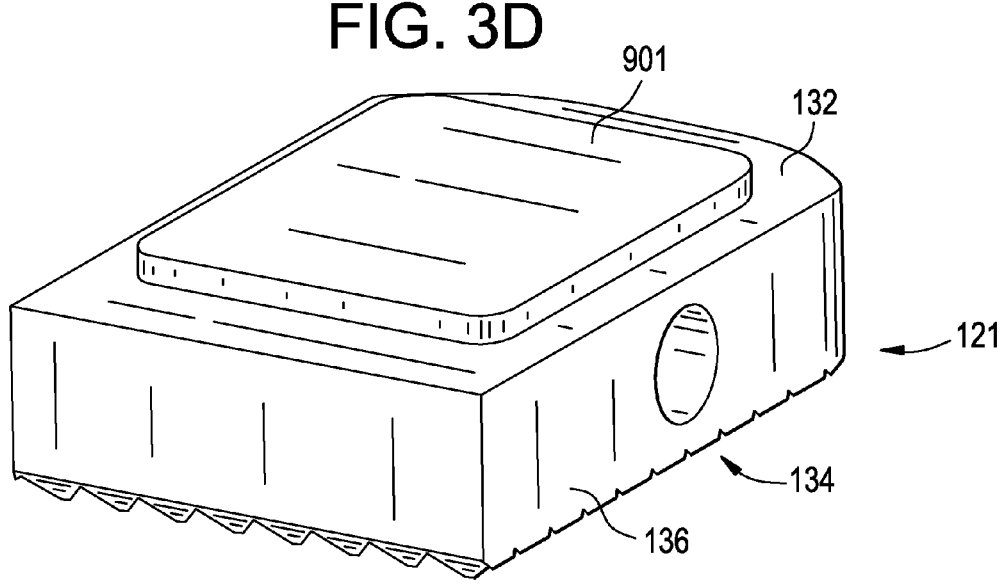
Figure 4A:
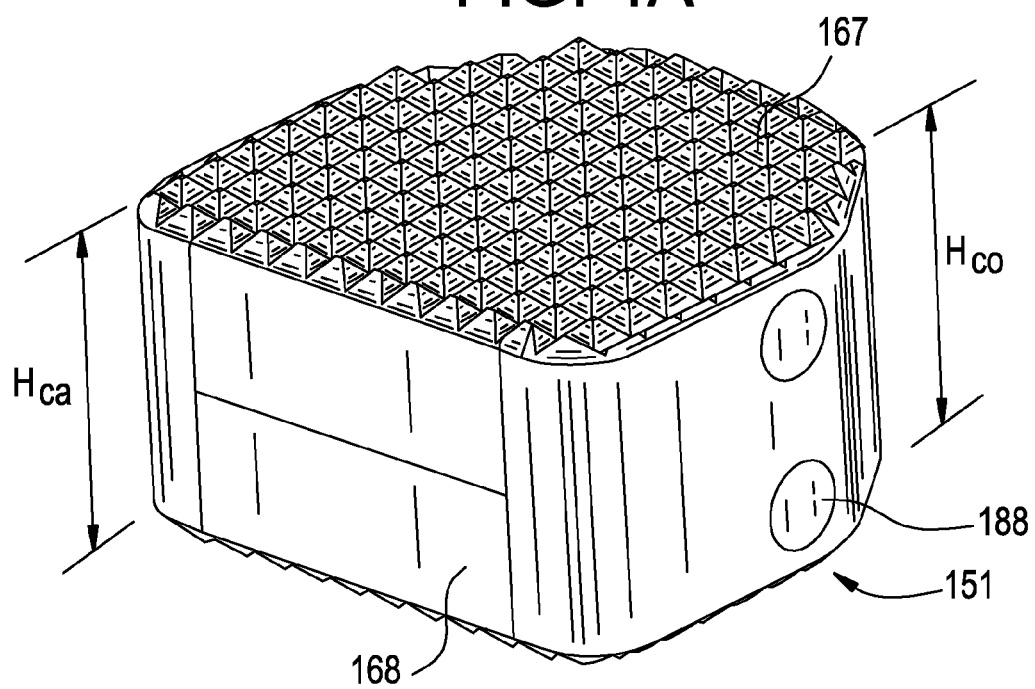
FIGS. 4A-4D disclose a fourth embodiment of the present invention.
Figure 4B:
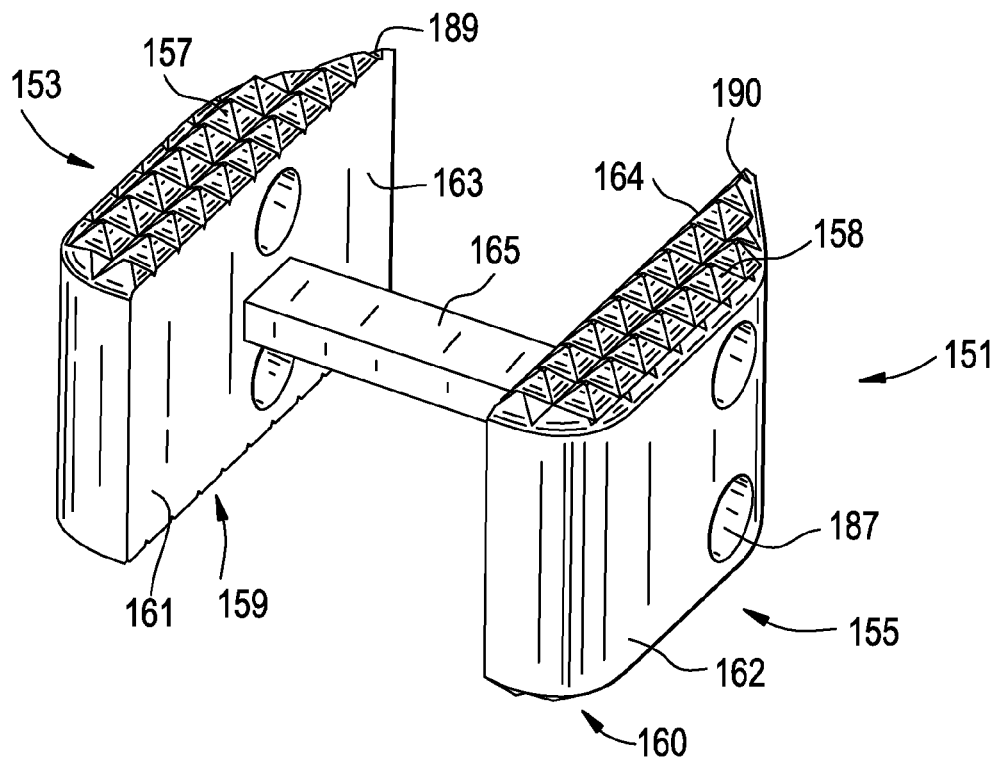
Figure 4C:
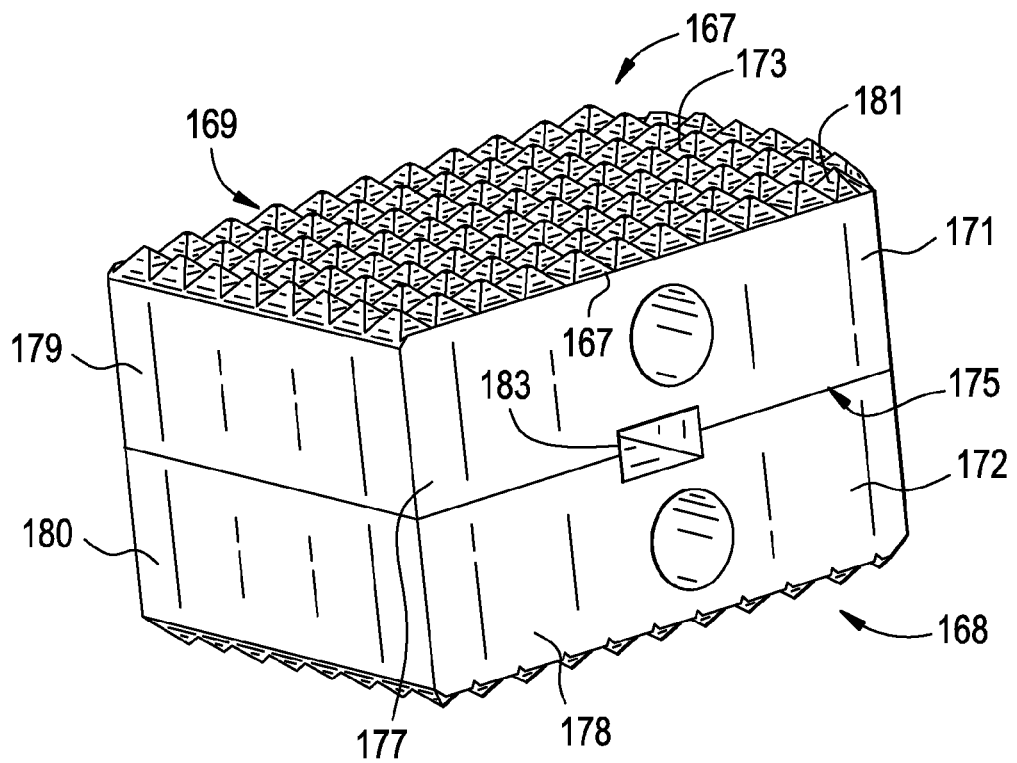
Figure 4D:
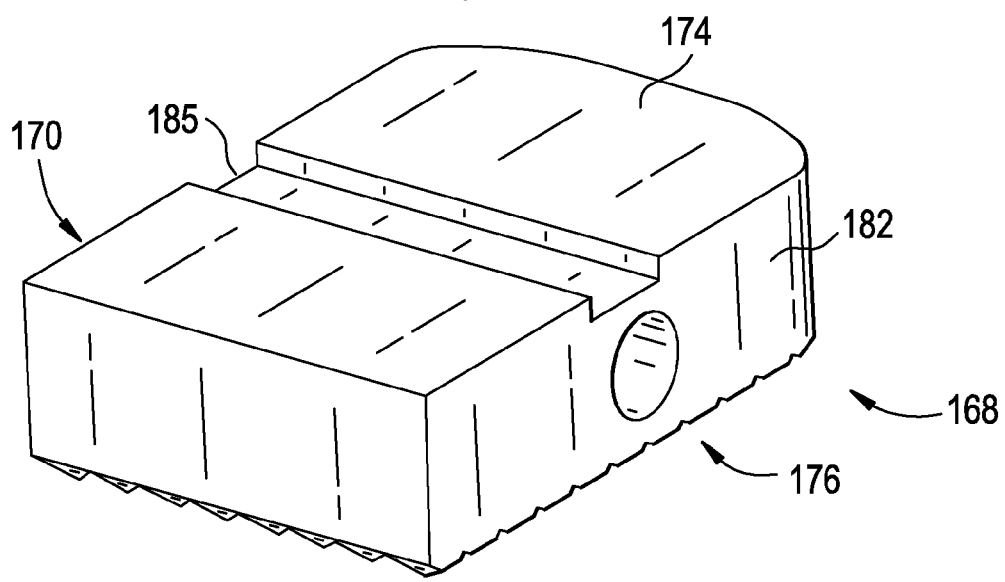

Now referring to FIGS. 2A-2C, there is provided an allograft composite spacer, comprising:

a) an integral cortical component 51 comprising:
  i. first 53 and second 55 opposing walls, each wall having an upper surface 57,58 and a lower surface 59,60 defining a height Hco therebetween, a first end portion 61 and a second end portion 63 and
  ii. a strut 65 extending from the first end portion of the first cortical wall to the first end portion of the second cortical wall, wherein the strut does not extend to either the upper surface or the lower surface, wherein the strut runs substantially from the first end portion to the second end portion of each opposing wall, b) upper 67 and lower 69 cancellous components, each having first 71,72 and second 73,74 lateral surfaces, an upper surface 75,76, a lower surface 77,78, a first end 79,80 having a first end surface 81,82, and a second end 83,84 wherein the upper cancellous component is received above the strut and between the opposing walls, and wherein the lower cancellous component is received below the strut and between the opposing walls.

In some embodiments, the second end portions of the first and second opposing walls of the cortical component each include a throughhole 85, wherein the through holes are aligned. Likewise, the cancellous portion has throughholes 86.

In some embodiments, the spacer further comprises:
  c) an allograft pin (88) inserted into both of the aligned throughholes.

In some embodiments, the second end portion of the first and second opposing walls of the cortical component has a second end face 87, and the second end portion of each opposing sidewall of the cortical component narrows towards the second endface.

In some embodiments, the upper and lower surfaces of the opposing walls of the cortical component each has gripping features thereon.

In some embodiments, the upper and lower surfaces of the cancellous component each has gripping features thereon.

In some embodiments, the upper and lower surfaces of the cortical component define a height Hco therebetween, the upper and lower surfaces of the cancellous component define a height Hca therebetween, and the height of cortical component is less than the height of the combined cancellous components.

In some embodiments, the strut is located in a middle third of the height between the upper and lower surfaces of each opposing wall.

Now referring to FIGS. 3A-3D, there is provided an allograft composite spacer, comprising:
a) an integral cortical component 101 comprising:
  i. first 103 and second 105 opposing walls, each wall having an upper surface 107,108 and a lower surface 109,110 defining a height Hco therebetween, a first end portion 111 and a second end portion 113, and
  ii. a strut 115 extending from the first end portion of the first cortical wall to the first end portion of the second cortical wall, wherein the strut does not extend to either the upper surface or the lower surface, wherein the strut runs substantially from the first end portion to the second end portion of each opposing wall, the strut having a vertical throughhole 117 therethrough,
b) upper 119 and lower 121 cancellous components, each having first 123,125 and second 127,129 lateral surfaces, an upper surface 131,132, a lower surface, 133, 134, a first end 135,136 having a first end surface 137,139, a second end 140,141, the upper cancellous component having an extension 143 extending from its lower surface, the lower cancellous component having an extension 901 extending from its upper surface
  wherein the upper cancellous component is received substantially above the strut and between the opposing walls, and
  wherein the lower cancellous component is received substantially below the strut and between the opposing walls, and
  wherein each extension is received in the vertical throughhole.

In some embodiments, the second end portions of the first and second opposing walls of the cortical component each include a throughhole 145, wherein the through holes are aligned. Likewise, the cancellous component has throughholes 144.

In some embodiments, the spacer further comprises:
c) an allograft pin 146 inserted into both of the aligned throughholes.

In some embodiments, the second end portion of the first and second opposing walls of the cortical component has a second end face 147,148, and the second end portion of each opposing sidewall of the cortical component narrows towards the second endface.

In some embodiments, the upper and lower surfaces of the opposing walls of the cortical component each has gripping features thereon.

In some embodiments, the upper and lower surfaces of the cancellous component each has gripping features thereon.

In some embodiments, the upper and lower surfaces of the cortical component define a height Hco therebetween, the upper and lower surfaces of the cancellous component define a height Hca therebetween, and the height of cortical component is substantially equal to the height of the combined cancellous components.

In some embodiments, the strut is located in a middle third of the height between the upper and lower surfaces of each opposing wall.

In some embodiments, the extension of the upper cancellous component contacts the extension of the lower cancellous component.

Now referring to FIGS. 4A-4D, there is provided an allograft composite spacer, comprising:
a) an integral cortical component 151 comprising:
  i. first 153 and second 155 opposing walls, each wall having an upper surface 157,158, a lower surface, 159,160, a first end portion 161,162 and a second end portion 163,164 and
  ii. a strut 165 extending from the first end portion of the first cortical wall to the first end portion of the second cortical wall, wherein the strut does not extend to either the upper surface or the lower surface, and
b) upper 167 and lower 168 cancellous components, each having first 169,170 and second 171,172 lateral surfaces, an upper surface 173,174, a lower surface 175, 176, a first end 177,178 having a first end surface 179,180, a second end 181,182, the upper cancellous component having a recess 183 on its lower surface running between its lateral surfaces, the lower cancellous component having a recess 185 on its upper surface running between its lateral surfaces,
  wherein the upper cancellous component is received between the opposing walls substantially above the strut and its recess receives the strut, and
  wherein the lower cancellous component is received between the opposing walls substantially below the strut and its recess receives the strut.

In some embodiments, the second end portions of the first and second opposing walls of the cortical component each include a throughhole 187, wherein the through holes are aligned.

In some embodiments, the spacer further comprises:
c) an allograft pin 188 inserted into both of the aligned throughholes.

In some embodiments, the second end portion of the first and second opposing walls of the cortical component has a second end face 189,190, and the second end portion of each opposing sidewall of the cortical component narrows towards the second endface.

In some embodiments, the upper and lower surfaces of the opposing walls of the cortical component each has gripping features thereon.

In some embodiments, the upper and lower surfaces of the cancellous component each has gripping features thereon.

In some embodiments, the upper and lower surfaces of the cortical component define a height Hco therebetween, the upper and lower surfaces of the cancellous component define a height Hca therebetween, and the height of cortical component is substantially equal to the height of the combined cancellous components.

In some embodiments, the strut is located in a middle third of the height between the upper and lower surfaces of each opposing wall.

In some embodiments, the upper cancellous component contacts the lower cancellous component.

Figure 5A:
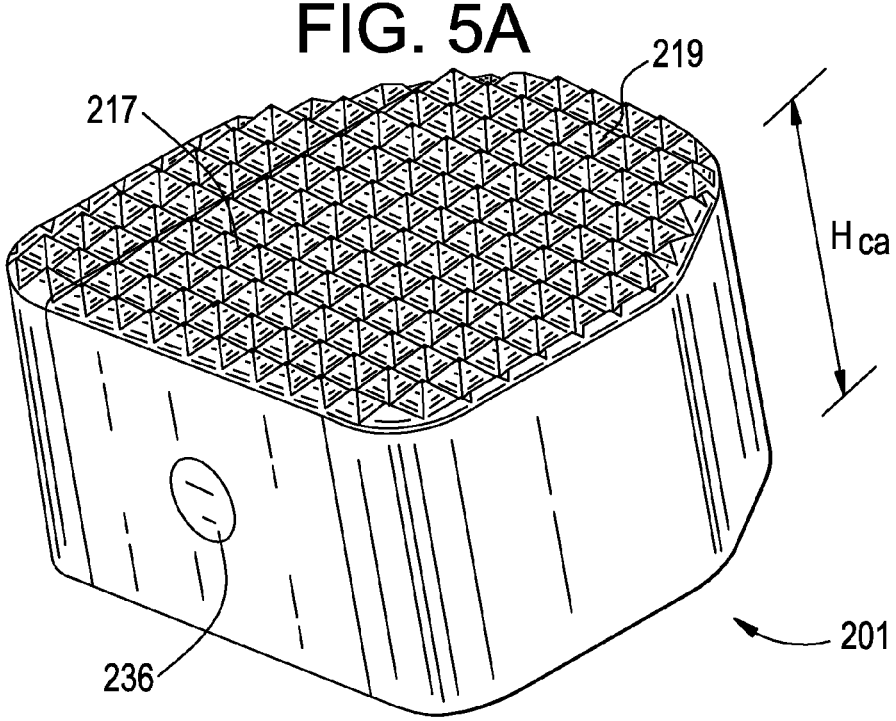
Figure 5B:
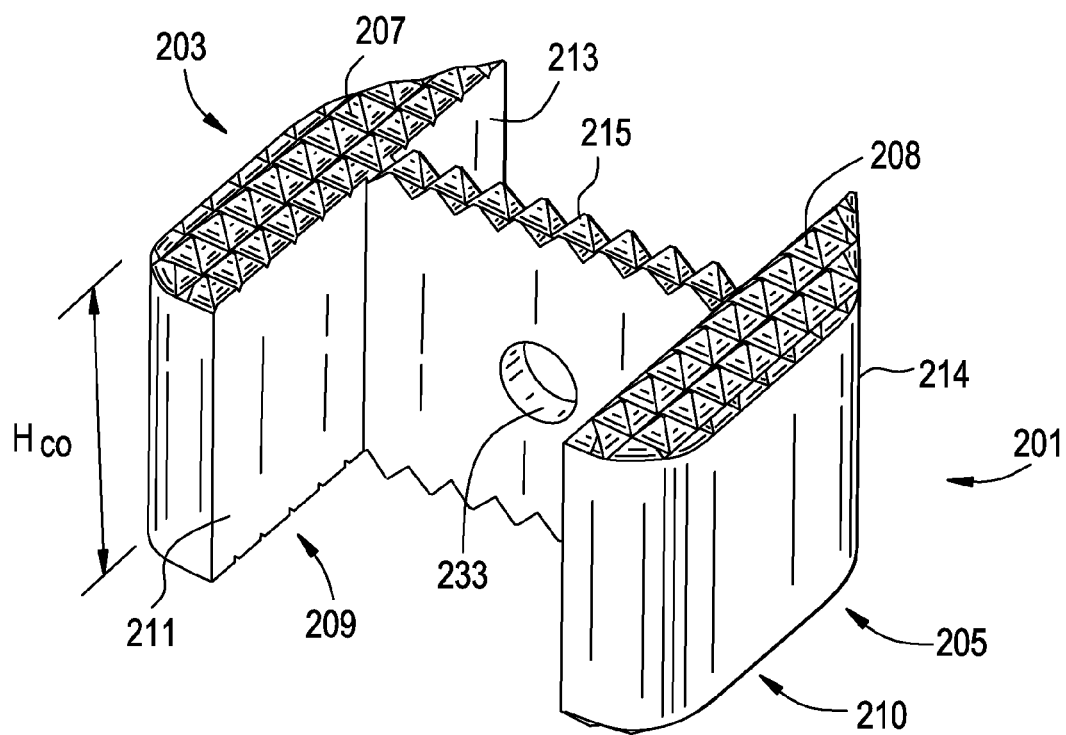

Now referring to FIGS. 5A-5C, there is provided an allograft composite spacer, comprising:
a) an integral cortical component 201 comprising:
  i. first 203 and second 205 opposing walls, each wall having an upper surface 207,208 and a lower surface 209,210 defining a height Hco therebetween, and an anterior end 211,212 and a posterior end 213,214 defining a middle third portion therebetween, and ii. a strut 215 extending between the opposing walls and extending substantially to each of the upper surface or the lower surface, and wherein the strut is located only in the middle third portion of the opposing walls, b) first 217 and second 219 cancellous components, each having first 221, 222 and second 223,224 lateral surfaces, an upper surface 225,226, a lower surface 227, 228, an anterior end 229,230 and a posterior end 231, 232, wherein the first cancellous component is received anterior to the strut and between the opposing walls, and wherein the second cancellous component is received posterior to the strut and between the opposing walls.

In some embodiments, the strut and the cancellous components each have a throughhole 233, 234 and the throughholes are aligned.

In some embodiments, the spacer further comprising:

c) an allograft pin 236 inserted through the aligned throughholes.

In some embodiments, each opposing sidewall of the cortical component narrows towards the anterior end.

In some embodiments, the upper and lower surfaces of the opposing walls of the cortical component each has gripping features thereon.

In some embodiments, the upper and lower surfaces of the cancellous component each has gripping features thereon.

In some embodiments, wherein the upper and lower surfaces of the cortical component define a height Hco therebetween, the upper and lower surfaces of each cancellous component define a height Hca therebetween, and the height of cortical component is substantially equal to the height of each cancellous component.

Because most of the load bearing of implant occurs on the cortical component, the effectiveness of teeth formed in the cortical component to grip into the surfaces of the vertebrae is enhanced. The application of force on the cortical component, and therefore the teeth, enhances the ability of the teeth to penetrate into and grip the vertebrae surfaces, thus preventing short-term slippage of the implant until the implant is fused with the vertebrae by the growth of new bone.

In some embodiments, the majority of toothed sections are comprised of the entire superior surface and inferior surface of the cortical components. Because these teeth 900 are preferably formed from cortical bone, they have sufficient strength and hardness to impale themselves into the vertebrae surfaces and provide an enhanced interlock with the adjacent vertebrae. However, teeth 900 may also be formed in cancellous components in order to simplify the manufacturing process, although these teeth do not have the same strength and hardness of teeth formed in cortical components.

Teeth are generally arranged in a two-dimensional array or pattern of three or four sided pyramids. In a preferred embodiment, teeth are arranged in an array composed of evenly spaced rows and columns. However, it can be readily seen by those skilled in the art that teeth may be arranged within toothed sections in many different ways, without departing from the spirit and scope of the present invention.

In preferred embodiments, the upper and lower surfaces of the cortical components are parallel with each other. However, in certain areas of the spine, it may be desirable for the implant to have inclined and/or curved surfaces in order to restore the natural curvature of the spine after the affected disc has been removed. Preferably, the angle of curvature between the upper and lower surfaces of the cortical components is between 5 and 20 degrees, thereby mimicing the natural lordosis of the spine.

In making the implants of the present invention, the cortical and cancellous components are first fabricated out of long bone. Holes for the required pins are then formed in respective components. Next, the cortical and cancellous components are assembled together as shown in the FIGS, and a pin is inserted through the respective. If desired, adhesive may be used between the cortical and cancellous components. In a preferred embodiment, the pin is sized so that there is a slight interference between the exterior surface of the pin and the holes into which it fits. The pin is thus secured in the holes by an interference fit between the pin and the holes. Alternatively, an adhesive may be used to secure the pin into the holes. Flat sections of the upper and lower surfaces, and of the implant exterior surface are then shaped into the proper desired form. Finally, teeth are formed into the upper and lower surfaces. In a preferred embodiment, the shaping of the components and sections of the implant is performed by computer-controlled milling. However, alternative methods of forming the various components of the implant may also be used.

In other embodiments, the cortical and cancellous blanks are assembled, the appropriate holes are drilled through the blanks, and then the appropriate pins are inserted into the drilled holes.

Although the implants shown in the FIGS. are sized and shaped to fit the cervical spine, implants of the present invention can be sized and shaped to fit the cervical, thoracic or lumbar portions of the spine.

The use of the implant according to the present invention will now be described using an anterior cervical interbody fusion as an example. As the implant according to the present invention conforms in size and shape to a portion of the vertebral, preoperative planning is recommended for proper sizing. Determine the appropriate implant height by measuring adjacent intervertebral discs on a lateral radiograph. The implant must be seated firmly with a tight fit between end plates when the segment is fully distracted. The tallest possible implant should be used to maximize segmental stability. Due to variability in degrees of magnification from radiographs, the measurements are only an estimate.

With the patient in a supine position and neck extended, radiographic equipment can assist in confirming the precise intraoperative position of the implant. The exposure is made via a transverse "hemi-collar" incision parallel to the clavicle; appropriate vertebral bodies are accessed through fascia incisions, muscle splitting, and blunt dissection. Retraction of the longus coli muscle is accomplished with a blunt toothed retractor placed medial-lateral and smooth bladed retractor positioned superior-inferior. The disc space is distracted with a Caspar pin distractor where the pins positioned parallel in the vertebra above and below the affected disc. Anterior osteophytes overhanging the disc space may need to be removed with a rongeur or osteotome. The disc, including cartilaginous endplates, is removed with cautery, pituitary rongeurs, and curettes. If necessary, posterior osteophytes can be removed. Rasps either in the form of trial or endplate are used to flatten the vertebral endplates and ensure all cartilage has been removed. Subchondral bone should be preserved as much as possible to function as a bearing surface for the interbody spacer.

An appropriately sized trial is used to determine both the height and footprint size of the required spacer. The trail also ensures the endplates are flat and at the correct angle. A slight amount of distraction (<2 mm) is helpful for inserting an allograft spacer as impact from insertion can cause fractures in the implant. The spacer is implanted and positioned with an inserter, distraction is released, the Caspar pins removed, and the correct placement of the spacer is confirmed. The Caspar pins are filled with bone wax and if additional stability is required supplemental fixation in the form of an anterior cervical plate can be placed prior to closing.

In some embodiments, the allograft can be encircled in a metallic annulus, thereby providing for greater strength. In some embodiments, the metallic ring has a height which is the same as the height of the cortical piece. In some embodiments, the metallic ring has a height which is less than the height of the cortical piece. In some embodiments, the metallic ring has a height which is greater than the height of the cortical piece.

While it is apparent that the illustrative embodiments of the invention herein disclosed fulfill the objectives stated above, it will be appreciated that numerous modifications and other embodiments may be devised by those skilled in the art. Therefore, it will be understood that the appended claims are intended to cover all such modifications and embodiments which come within the spirit and scope of the present invention.

We claim:

1. An allograft composite spacer, comprising:
   a) an integral cortical component comprising:
      i. first and second opposing walls, each wall having an upper surface, a lower surface, a first end portion and a second end portion and
      ii. a strut extending from the first end portion of the first cortical wall to the first end portion of the second cortical wall, wherein the strut does not extend to either the upper surface or the lower surface, and
   b) a cancellous component having first and second lateral surfaces, an upper surface, a lower surface, a first end have a first end surface, a second end, and a recess in the first end surface extending from the first lateral surface to the second lateral surface,
   wherein the strut of the cortical components is received in the recess of the cancellous component.

2. The spacer of claim 1 wherein the second end portions of the first and second opposing walls of the cortical component each include a throughhole, wherein the through holes are aligned.

3. The spacer of claim 2 further comprising:
   c) an allograft pin inserted into both of the aligned throughholes.

4. The spacer of claim 1 wherein the second end portion of the first and second opposing walls of the cortical component has a second end face, and the second end portion of each opposing sidewall of the cortical component narrows towards the second endface.

5. The spacer of claim 1 wherein the upper and lower surfaces of the opposing walls of the cortical component each has gripping features thereon.

6. The spacer of claim 1 wherein the upper and lower surfaces of the cancellous component each has gripping features thereon.

7. The spacer of claim 1 wherein the upper and lower surfaces of the cortical component define a height therebetween, the upper and lower surfaces of the cancellous component define a height therebetween, and the height of cortical component is substantially equal to the height of the cancellous component.

8. An allograft composite spacer, comprising:
   a) an integral cortical component comprising:
      i. first and second opposing walls, each wall having an upper surface and a lower surface defining a height therebetween, a first end portion and a second end portion and
      ii. a strut extending from the first end portion of the first cortical wall to the first end portion of the second cortical wall, wherein the strut does not extend to either the upper surface or the lower surface, wherein the strut runs substantially from the first end portion to the second end portion of each opposing wall,
   b) upper and lower cancellous components, each having first and second lateral surfaces, an upper surface, a lower surface, a first end have a first end surface, a second end,
   wherein the upper cancellous component is received above the strut and between the opposing walls, and
   wherein the lower cancellous component is received below the strut and between the opposing walls.

9. The spacer of claim 8 wherein the second end portions of the first and second opposing walls of the cortical component each include a throughhole, wherein the through holes are aligned.

10. The spacer of claim 9 further comprising:
    c) an allograft pin inserted into both of the aligned throughholes.

11. The spacer of claim 8 wherein the second end portion of the first and second opposing walls of the cortical component has a second end face, and the second end portion of each opposing sidewall of the cortical component narrows towards the second endface.

12. The spacer of claim 8 wherein the upper and lower surfaces of the opposing walls of the cortical component each has gripping features thereon.

13. The spacer of claim 8 wherein the upper and lower surfaces of the cancellous component each has gripping features thereon.

14. The spacer of claim 8 wherein the upper and lower surfaces of the cortical component define a height therebetween, the upper and lower surfaces of the cancellous component define a height therebetween, and the height of cortical component is less than the height of the combined cancellous components.

15. The spacer of claim 11 wherein the strut is located in a middle third of the height between the upper and lower surfaces of each opposing wall.

16. An allograft composite spacer, comprising:
    a) an integral cortical component comprising:
       i. first and second opposing walls, each wall having an upper surface and a lower surface defining a height therebetween, a first end portion and a second end portion and
       ii. a strut extending from the first end portion of the first cortical wall to the first end portion of the second cortical wall, wherein the strut does not extend to either the upper surface or the lower surface, wherein the strut runs substantially from the first end portion to the second end portion of each opposing wall, the strut having a vertical throughhole therethrough
    b) upper and lower cancellous components, each having first and second lateral surfaces, an upper surface, a lower surface, a first end have a first end surface, a second end, the upper cancellous component having an extension extending from its lower surface, the lower cancellous component having an extension extending from its upper surface wherein the upper cancellous component is received substantially above the strut and between the opposing walls, and wherein the lower cancellous component is received substantially below the strut and between the opposing walls, and wherein each extension is received in the vertical throughhole.

17. The spacer of claim 16 wherein the second end portions of the first and second opposing walls of the cortical component each include a throughhole, wherein the through holes are aligned.

18. The spacer of claim 17 further comprising:
   c) an allograft pin inserted into both of the aligned throughholes.

19. The spacer of claim 16 wherein the second end portion of the first and second opposing walls of the cortical component has a second end face, and the second end portion of each opposing sidewall of the cortical component narrows towards the second endface.

20. The spacer of claim 16 wherein the upper and lower surfaces of the opposing walls of the cortical component each has gripping features thereon.

21. The spacer of claim 16 wherein the upper and lower surfaces of the cancellous component each has gripping features thereon.

22. The spacer of claim 16 wherein the upper and lower surfaces of the cortical component define a height therebetween, the upper and lower surfaces of the cancellous component define a height therebetween, and the height of cortical component is substantially equal to the height of the combined cancellous components.

23. The spacer of claim 16 wherein the strut is located in a middle third of the height between the upper and lower surfaces of each opposing wall.

24. The spacer of claim 16 wherein the extension of the upper cancellous component contacts the extension of the lower cancellous component.

25. An allograft composite spacer, comprising:
   a) an integral cortical component comprising:
      i. first and second opposing walls, each wall having an upper surface, a lower surface, a first end portion and a second end portion and
      ii. a strut extending from the first end portion of the first cortical wall to the first end portion of the second cortical wall, wherein the strut does not extend to either the upper surface or the lower surface, and
   b) upper and lower cancellous components, each having first and second lateral surfaces, an upper surface, a lower surface, a first end have a first end surface, a second end, the upper cancellous component having a recess on its lower surface running between its lateral surfaces, the lower cancellous component having a recess on its upper surface running between its lateral surfaces, wherein the upper cancellous component is received between the opposing walls substantially above the strut and its recess receives the strut, and wherein the lower cancellous component is received between the opposing walls substantially below the strut and its recess receives the strut.

26. The spacer of claim 25 wherein the second end portions of the first and second opposing walls of the cortical component each include a throughhole, wherein the through holes are aligned.

27. The spacer of claim 26 further comprising:
   c) an allograft pin inserted into both of the aligned throughholes.

28. The spacer of claim 25 wherein the second end portion of the first and second opposing walls of the cortical component has a second end face, and the second end portion of each opposing sidewall of the cortical component narrows towards the second endface.

29. The spacer of claim 25 wherein the upper and lower surfaces of the opposing walls of the cortical component each has gripping features thereon.

30. The spacer of claim 25 wherein the upper and lower surfaces of the cancellous component each has gripping features thereon.

31. The spacer of claim 25 wherein the upper and lower surfaces of the cortical component define a height therebetween, the upper and lower surfaces of the cancellous component define a height therebetween, and the height of cortical component is substantially equal to the height of the combined cancellous components.

32. The spacer of claim 25 wherein the strut is located in a middle third of the height between the upper and lower surfaces of each opposing wall.

33. The spacer of claim 25 wherein the upper cancellous component contacts the lower cancellous component.

34. An allograft composite spacer, comprising:
   a) an integral cortical component comprising:
      i. first and second opposing walls, each wall having an upper surface and a lower surface defining a height therebetween, and an anterior end and a posterior end defining a middle third portion therebetween, and
      ii. a strut extending between the opposing walls and extending substantially to each of the upper surface or the lower surface, and wherein the strut is located only in the middle third portion of the opposing walls,
   b) first and second cancellous components, each having first and second lateral surfaces, an upper surface, a lower surface, an anterior end and a posterior end, wherein the first cancellous component is received anterior to the strut and between the opposing walls, and wherein the second cancellous component is received posterior to the strut and between the opposing walls.

35. The spacer of claim 34 wherein the strur and the cancellous components each have a throughhole, wherein the throughholes are aligned.

36. The spacer of claim 35 further comprising:
   c) an allograft pin inserted through the aligned throughholes.

37. The spacer of claim 34 wherein each opposing sidewall of the cortical component narrows towards the anterior end.

38. The spacer of claim 34 wherein the upper and lower surfaces of the opposing walls of the cortical component each has gripping features thereon.

39. The spacer of claim 34 wherein the upper and lower surfaces of the cancellous component each has gripping features thereon.

40. The spacer of claim 34 wherein the upper and lower surfaces of the cortical component define a height therebetween, the upper and lower surfaces of each cancellous component define a height therebetween, and the height of cortical component is substantially equal to the height of each cancellous component.

* * * * *